(12) United States Patent
Shimamura et al.

(10) Patent No.: US 11,065,025 B2
(45) Date of Patent: Jul. 20, 2021

(54) PROBE, TREATMENT INSTRUMENT AND TREATMENT DEVICE

(71) Applicant: OLYMPUS CORPORATION, Hachioji (JP)

(72) Inventors: Yukihiko Shimamura, Yoshikawa (JP); Masashi Yamada, Sagamihara (JP); Hideyuki Komamura, Kamiina-gun (JP); Tomokazu Shimizu, Kamiina-gun (JP)

(73) Assignee: OLYMPUS CORPORATION, Tokyo (JP)

( * ) Notice: Subject to any disclaimer, the term of this patent is extended or adjusted under 35 U.S.C. 154(b) by 233 days.

(21) Appl. No.: 16/244,771

(22) Filed: Jan. 10, 2019

(65) Prior Publication Data

US 2019/0142450 A1 May 16, 2019

Related U.S. Application Data

(63) Continuation of application No. PCT/JP2016/070584, filed on Jul. 12, 2016.

(51) Int. Cl.
*A61B 17/32* (2006.01)
*A61B 17/00* (2006.01)
(Continued)

(52) U.S. Cl.
CPC ...... *A61B 17/320068* (2013.01); *A61B 17/00* (2013.01); *A61B 17/32* (2013.01);
(Continued)

(58) Field of Classification Search
CPC .... A61B 17/320068; A61B 17/320092; A61B 2017/320073; A61B 2017/320088;
(Continued)

(56) References Cited

U.S. PATENT DOCUMENTS

| 5,776,155 A | 7/1998 | Beaupre et al. |
| 5,938,633 A | 8/1999 | Beaupre |

(Continued)

FOREIGN PATENT DOCUMENTS

| CN | 102186429 A | 9/2011 |
| JP | H04-156845 A | 5/1992 |

(Continued)

OTHER PUBLICATIONS

Oct. 11, 2016 International Search Report issued in International Patent Application PCT/JP2016/070584.
(Continued)

*Primary Examiner* — Melanie E Tyson

(74) *Attorney, Agent, or Firm* — Oliff PLC

(57) ABSTRACT

A probe configured to be connected to a transducer unit configured to generate ultrasonic vibration, includes an elongated vibration transmission portion configured to transmit the ultrasonic vibration; and an engagement member provided on and/or near an outer circumference at a position which becomes a node of the ultrasonic vibration when the ultrasonic vibration is transmitted to the vibration transmission portion, the engagement member being formed by a material of an identical to or smaller damping rate than a damping rate of the ultrasonic vibration in the vibration transmission portion, and the engagement member being engaged with an exterior member disposed on an outer side of the vibration transmission portion.

20 Claims, 17 Drawing Sheets

(51) Int. Cl.
  *A61L 31/02* (2006.01)
  *A61B 17/295* (2006.01)
(52) U.S. Cl.
  CPC ............ *A61L 31/022* (2013.01); *A61B 17/295* (2013.01); *A61B 2017/320089* (2017.08); *A61B 2017/320094* (2017.08)
(58) Field of Classification Search
  CPC ....... A61B 2017/320089; A61B 2017/320094; A61L 31/022
  See application file for complete search history.

(56) References Cited

U.S. PATENT DOCUMENTS

| | | | |
|---|---|---|---|
| 5,971,949 | A | 10/1999 | Levin et al. |
| 6,159,176 | A | 12/2000 | Broadwin et al. |
| 2007/0106158 | A1 | 5/2007 | Madan et al. |
| 2009/0036912 | A1* | 2/2009 | Wiener ............... A61B 17/2202 606/169 |
| 2011/0201887 | A1 | 8/2011 | Greenblatt et al. |
| 2017/0021199 | A1 | 1/2017 | Sanai et al. |

FOREIGN PATENT DOCUMENTS

| | | |
|---|---|---|
| JP | H04-156846 A | 5/1992 |
| JP | H09-98980 A | 4/1997 |
| JP | 2000-506430 A | 5/2000 |
| JP | 2000-508957 A | 7/2000 |
| JP | 2009-511206 A | 3/2009 |
| JP | 2010-167084 A | 8/2010 |
| JP | 2010-535089 A | 11/2010 |
| JP | 2014-144147 A | 8/2014 |
| WO | 2016/035380 A1 | 3/2016 |

OTHER PUBLICATIONS

Nov. 19, 2019 Office Action issued in Japanese Patent Application No. 2018-527295.
Jan. 15, 2019 International Preliminary Report on Patentability issued in International Patent Application PCT/ JP2016/070584.
Dec. 10, 2020 Office Action issued in Chinese Patent Application No. 201680087607.5.

\* cited by examiner

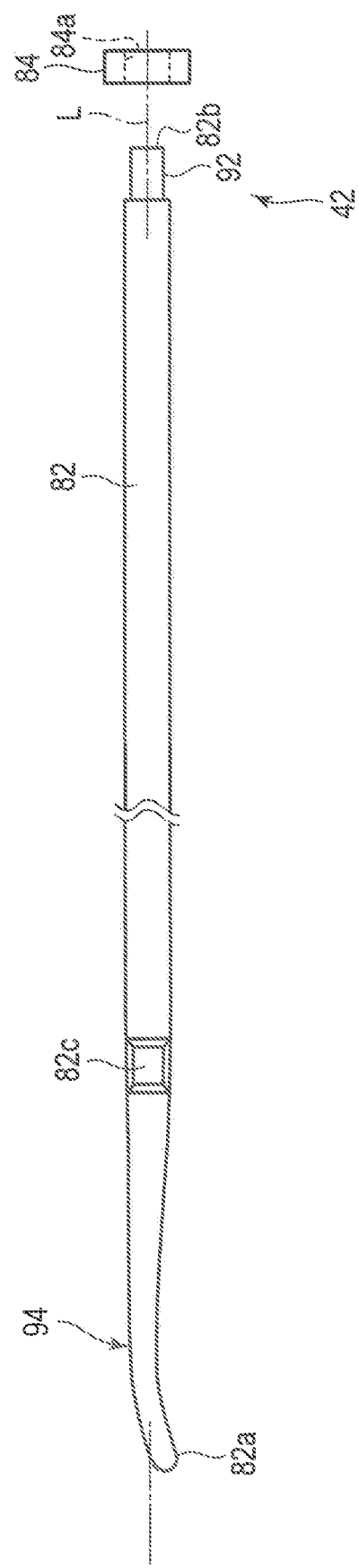

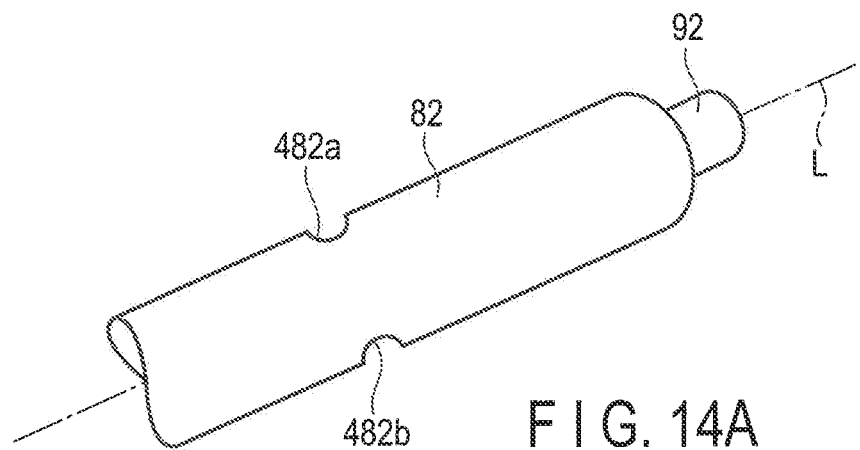
F I G. 14A
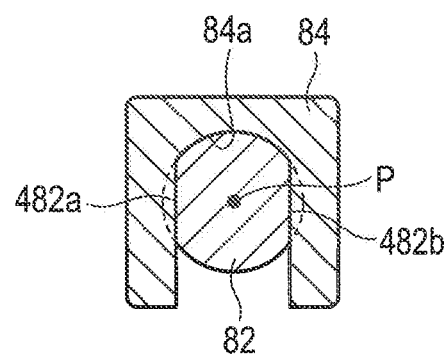
F I G. 14B
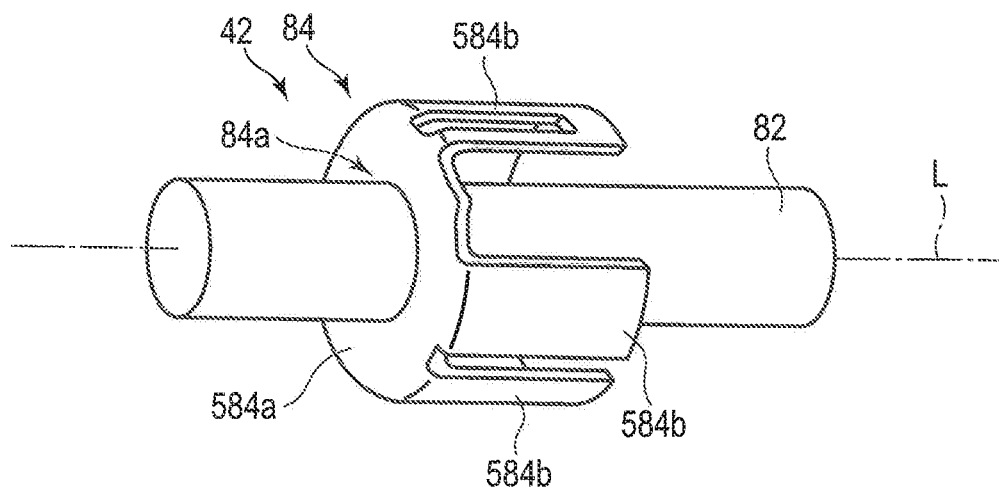
F I G. 15A

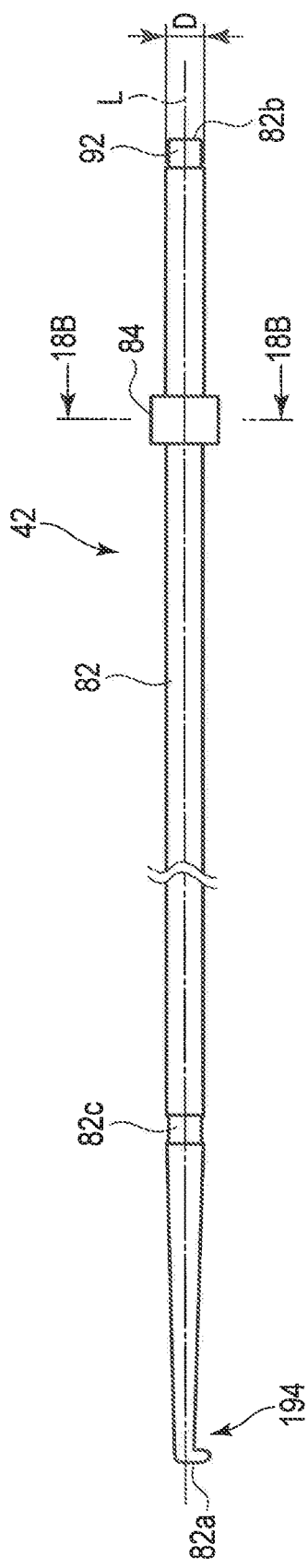
F I G. 18A

PROBE, TREATMENT INSTRUMENT AND TREATMENT DEVICE

CROSS-REFERENCE TO RELATED APPLICATIONS

This application is a Continuation Application of PCT Application No. PCT/JP2016/070584, filed Jul. 12, 2016, the entire contents of which are incorporated herein by reference.

BACKGROUND OF THE INVENTION

1. Field of the Invention

The present invention relates to a probe which can transmit ultrasonic vibration and is used to treat biological tissues, a treatment instrument which includes the probe and a treatment device which includes a treatment instrument.

2. Description of the Related Art

For example, Jpn. Pat. Appln. KOKAI Publication No. 2010-167084 discloses a probe to which ultrasonic vibration transmits. The probe is used to treat a biological body by using ultrasonic vibration. Hence, the probe has appropriate fracture resistance (strength), has a good acoustic property (vibration transmission property), and is integrally formed by a titanium material such as a titanium alloy material as one example of a material having bicompatibility.

The length of the probe is adjusted in relation to an oscillation frequency of an ultrasonic transducer. When vibration is transmitted to the probe, a plurality of antinode positions of vibration and a plurality of node positions of vibration are formed. At and near a position of an outer circumference at a position which becomes a node of vibration, an engagement portion which engages with an exterior member is formed. Consequently, the exterior member can be used to hold the probe.

BRIEF SUMMARY OF THE INVENTION

According to one aspect of the present invention, a probe configured to be connected to a transducer unit configured to generate ultrasonic vibration, includes: an elongated vibration transmission portion that is configured to transmit the ultrasonic vibration; and an engagement member that is provided on and/or near an outer circumference at a position which is a node of the ultrasonic vibration when the ultrasonic vibration is transmitted to the vibration transmission portion, the engagement member being formed by a material of an identical to or smaller damping rate than a damping rate of the ultrasonic vibration in the vibration transmission portion, and the engagement member being engaged with an exterior member disposed on an outer side of the vibration transmission portion.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is a schematic view illustrating a state where the vibration transmission portion of the probe of the shaft of the treatment instrument, and the engagement member are separated in the treatment system according to the first embodiment.

FIG. 14A is a schematic perspective view illustrating the vicinity of the proximal end portion of the vibration transmission member of the probe according to the modified example of the first embodiment.

FIG. 14B is a schematic cross-sectional view illustrating a state where the engagement member is fitted near the proximal end portion of the vibration transmission member illustrated in FIG. 14A.

FIG. 15A is a schematic perspective view illustrating a state where the engagement member is fixed near the proximal end portion of the vibration transmission member of the probe according to the modified example of the first embodiment.

FIG. 18A is a schematic view illustrating a state where an engagement member is fixed to an appropriate position of an outer circumference of a vibration transmission portion of a probe of a shaft of a treatment instrument in the treatment system according to the second embodiment.

DETAILED DESCRIPTION OF THE INVENTION

Embodiments for carrying out the present invention will be described below with reference to the drawings.

First Embodiment

First, a first embodiment will be described with reference to FIGS. 1 to 6.

Figure 1:
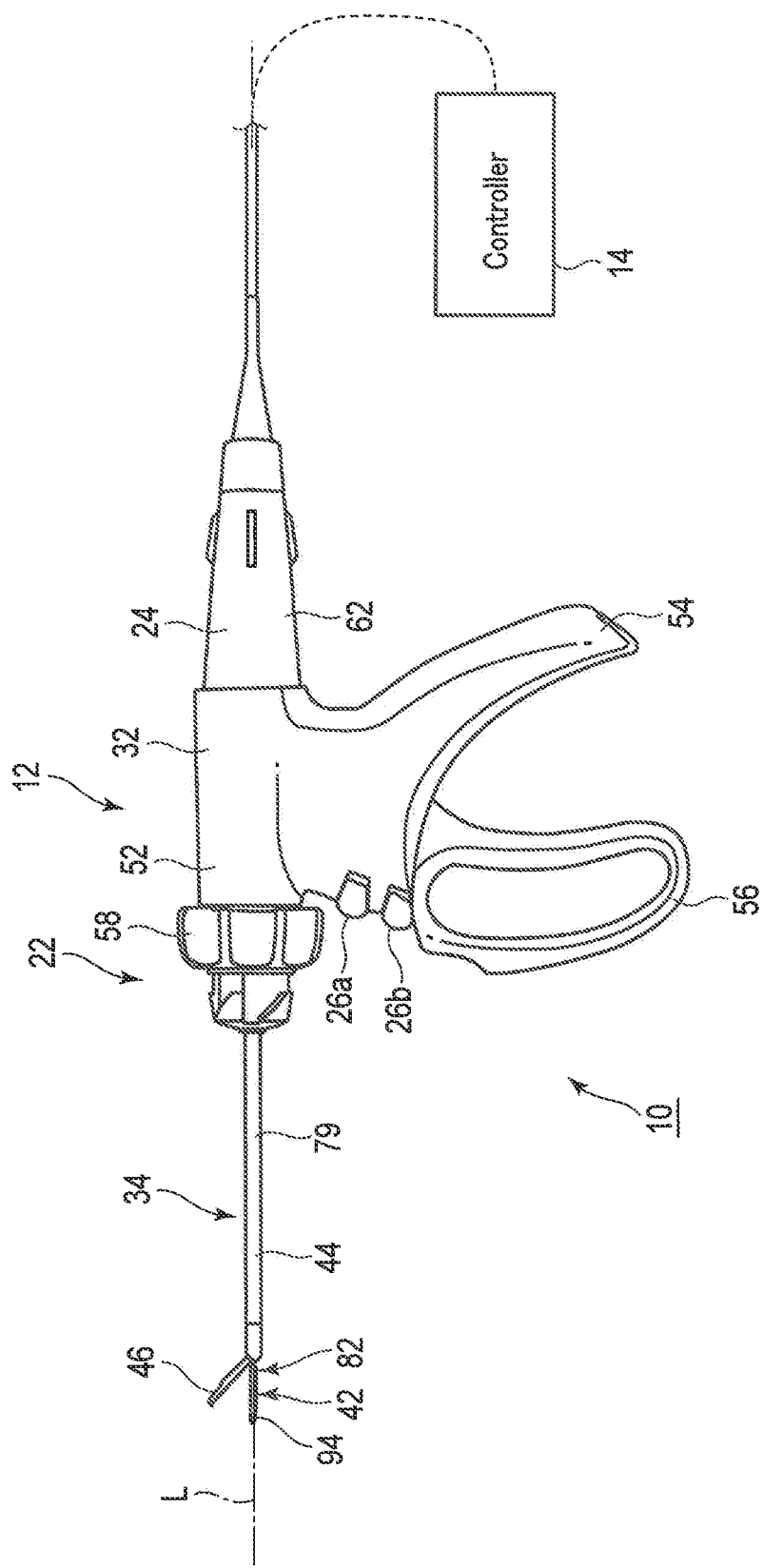
FIG. 1 is a schematic view illustrating a treatment system according to a first embodiment.

As illustrated in FIG. 1, a treatment system 10 includes a treatment device 12 and a controller 14 which includes a power supply. An example where the treatment device 12 according to the present embodiment can treat biological tissues by ultrasonic vibration and high frequency energy will be described. Naturally, the treatment device 12 may be able to treat biological tissues only by ultrasonic vibration.

The treatment device 12 includes a treatment instrument 22, and a transducer unit 24 which is used in a state fixed to the treatment instrument 22. The transducer unit 24 includes a built-in transducer 64 described below, and is connected to the controller 14. Hence, when the electric power is supplied from the controller 14 to the transducer 64, it is possible for the transducer 64 of the transducer unit 24 to generate ultrasonic vibration of an appropriate frequency. Furthermore, the treatment instrument 22 and the transducer unit 24 can supply high frequency energy to a biological tissue between an elongated vibration transmission portion 82 described below, and a jaw 46 including a high frequency electrode described below by a known mechanism.

The treatment instrument 22 includes a first button 26a and a second button 26b. The first button 26a and the second button 26b are electrically connected to the controller 14 via the transducer unit 24. When, for example, the first button 26a is pressed, high frequency energy is outputted between high frequency electrodes described below in a state where the biological tissue is disposed therebetween. Hence, the treatment instrument 22, for example, stops bleeding from a blood vessel when the first button 26a is pressed. When the second button 26b is pressed, high frequency energy is outputted between the high frequency electrodes in a state where the biological tissue is disposed therebetween, and electric power which generates vibration is output to the transducer unit 24. Consequently, when the second button 26b is pressed, the treatment instrument 22 can perform incision mainly by a function of ultrasonic vibration while stopping the bleeding from the blood vessel mainly by high frequency energy.

The treatment instrument 22 includes a housing 32 including a shaft 34. The housing 32 is formed as a gripping portion gripped by a user such as a doctor. The housing 32 is formed by a resin material having an electrical insulation property.

The shaft 34 includes a probe 42, and a cylindrical portion (sheath) 44 which covers an outer circumference of the vibration transmission portion 82 of the probe 42 described below.

Figure 2:
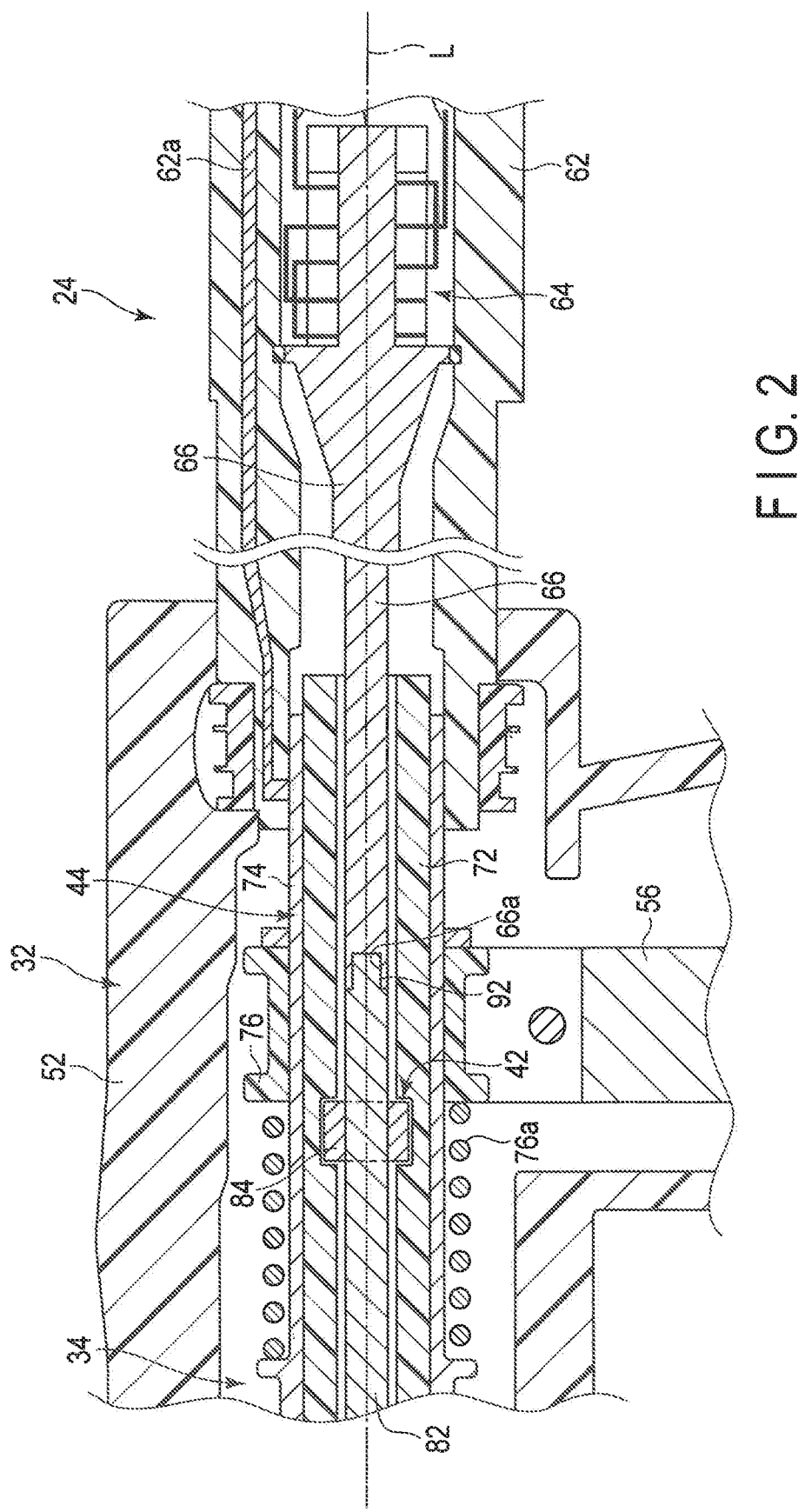
FIG. 2 is a schematic vertical cross-sectional view illustrating a state where a treatment instrument and a transducer unit are connected in the treatment system according to the first embodiment.

As illustrated in FIG. 2, the cylindrical portion 44 of the shaft 34 is supported in the housing 32. The cylindrical portion 44 is itself formed by a metal material such as a stainless steel material. An outer circumferential surface of the cylindrical portion 44 is likely to come into contact with a patient. Hence, the outer circumferential surface of the cylindrical portion 44 is coated by a resin material, and has an electrical insulation property.

The jaw 46 is supported at a distal end portion of the cylindrical portion 44 turnably around a pivotal axis perpendicular to an axial direction of a longitudinal axis L. A position of the jaw 46 is operated by a movable cylindrical portion 74 which is movable along the longitudinal axis L as described below. The movable cylindrical portion 74 is allowed by a slider 76 inside the housing 32 to move in conjunction with a movable handle 56 described below.

A portion of the jaw 46 which faces the vibration transmission portion 82 used as the high frequency electrode is provided with a high frequency electrode of a different pole from that of the vibration transmission portion 82.

In addition, an outer circumference of a portion of the movable cylindrical portion 74 which protrudes from a rotation knob 58 to a distal end side is covered by a cylindrical member 79 (see FIG. 1) made of a stainless steel material whose outer circumferential surface is applied an insulation coating. Although not illustrated, an inner cylindrical body is disposed between the vibration transmission portion 82 and the movable cylindrical portion 74. An outer circumferential surface at a position which becomes a node P of vibration on the outer circumferential surface of the vibration transmission portion 82 is provided with a rubber lining 83 (see FIG. 3A) used as a spacer disposed between the outer circumferential surface and an inner circumferential surface of the inner cylindrical body. In addition, a recess portion 82c is formed on the outer circumferential surface at a position to become the node P of vibration on the outer circumferential surface of the vibration transmission portion 82, and the recess portion 82c prevents movement of the rubber lining 83 along the longitudinal axis L.

Although description of the housing 32 is omitted as appropriate since the housing 32 is known, the housing 32 includes a main body (gripping body) 52 and a fixed handle 54 which is provided to the main body 52. The movable handle 56 is disposed in the housing 32. The movable handle 56 is biased apart from the fixed handle 54. In this case, the jaw 46 at the distal end of the cylindrical portion 44 is apart from an end effector 94 of the vibration transmission portion 82. The user (doctor) can place the movable handle 56 close to the fixed handle 54. In conjunction with this operation, the jaw 46 at the distal end of the cylindrical portion 44 turns around the pivotal axis perpendicular to the axial direction of the longitudinal axis L, and comes close to the end effector 94 of the vibration transmission portion 82.

Similarly, although description of the main body 52 is omitted as appropriate since the main body 52 is well known, the main body 52 of a cylindrical shape of the housing 32 is provided with a rotation operation knob 58 coaxially with the longitudinal axis L. The rotation knob 58 is rotatable around the longitudinal axis L with respect to the main body 52 of the housing 32. In this case, as described below, as the rotation knob 58 rotates, the cylindrical portion 44, the jaw 46 and the probe 42 rotate together. As the rotation knob 58 rotates, not only the cylindrical portion 44, the jaw 46 and the probe 42 but also the transducer unit 24 rotate together.

The transducer unit 24 includes a case 62, a transducer 64 which is disposed inside the case 62 and generates ultrasonic vibration when receiving a supply of electric power, and a transducer side transmission portion 66 which is fixed to the transducer 64, and transmits vibration (vertical vibration) generated by the transducer 64. A proximal end of the transducer side transmission portion 66 is fixed to the transducer 64. A connection portion 66a which is detachably fixed to the vibration transmission portion 82 is formed at a distal end of the transducer side transmission portion 66. In this case, the connection portion 66a is formed as a female screw. The connection portion 66a corresponds to an antinode of vibration when vibration is transmitted from the transducer 64.

The cylindrical portion (exterior member) 44 of the shaft 34 includes a holder (exterior member) 72 which is formed from a material having an electrical insulation property, and the movable cylindrical portion 74 which is provided on an outer side of the holder 72. The movable cylindrical portion 74 is formed by a conductive material, and is movable along the longitudinal axis L with respect to a transducer case 62 and the holder 72. The slider 76 formed from an insulation material is provided on an outer circumference of the movable cylindrical portion 74. The slider 76 is movable along the longitudinal axis L with respect to the movable cylindrical portion 74. The slider 76 and the movable cylindrical portion 74 are connected via elastic members 76a such as coil springs. Furthermore, the movable handle 56 is attached to the slider 76. By opening and closing the movable handle 56 with respect to the fixed handle 54, a driving force transmits to the slider 76, and the slider 76 moves along the longitudinal axis L. Furthermore, the driving force is transmitted from the slider 76 to the movable cylindrical portion 74 via the elastic members 76a, and the movable cylindrical portion 74 moves along the longitudinal axis L with respect to the transducer case 62 and the holder 72.

A conductive portion 62a is formed in the transducer case 62. The conductive portion 62a is electrically connected to the controller 14. Furthermore, in a state where the cylindrical portion 44 is connected to the transducer case 62, the movable cylindrical portion 74 of the cylindrical portion 44 movably comes into contact with the conductive portion 62a of the transducer case 62. Hence, in a state where the cylindrical portion 44 is connected to the transducer case 62, the transducer case 62 and the movable cylindrical portion 74 are electrically connected. Consequently, a high frequency current is supplied from the controller 14 to the movable cylindrical portion 74 of the cylindrical portion 44 via the conductive portion 62a of the transducer case 62. In addition, the conductive portion 62a of the transducer case 62 and the movable cylindrical portion 74 of the cylindrical portion 44 are electrically insulated from the vibration transmission portion 82.

Figure 3A:
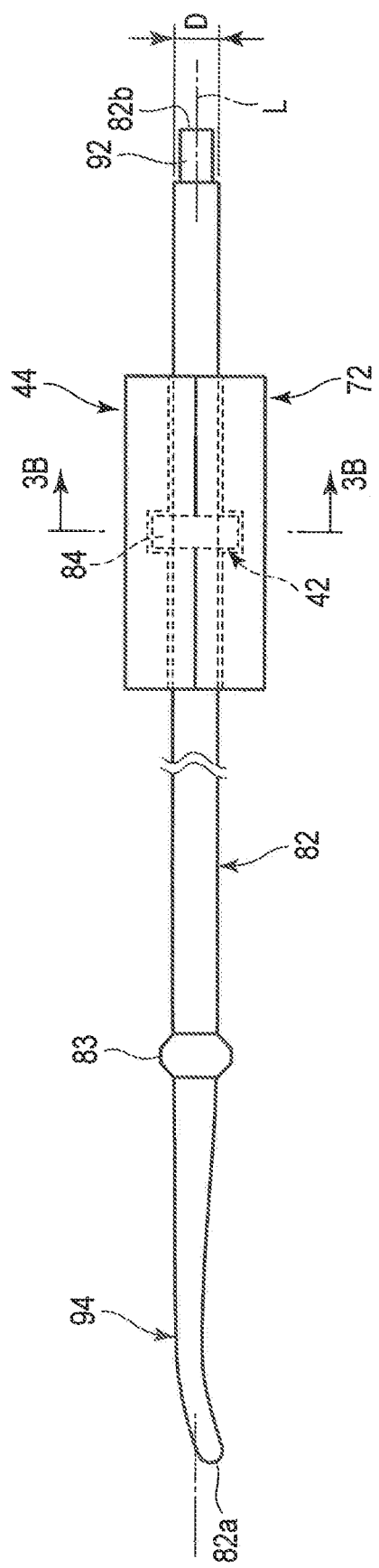
FIG. 3A is a schematic view illustrating a probe of a shaft of the treatment instrument and a holder of a cylindrical portion in the treatment system according to the first embodiment.

As illustrated in FIG. 3A, the probe 42 includes the vibration transmission portion (main body portion) 82 which is configured to transmit ultrasonic vibration generated by the transducer unit 24, and an engagement member 84 which is attached to an outside of the vibration transmission portion 82. The vibration transmission portion 82 is formed by appropriately machining a columnar rod (round bar) made of titanium or a titanium alloy material by taking into account a vibration transmission property, strength, a heat generation property biocompatibility or the like. An example where an α-β titanium alloy material such as a Ti-6Al-4V alloy is used for the vibration transmission portion 82 will be described. The columnar rod defines a maximum outer diameter D of the vibration transmission portion 82.

A distal end 82a and a proximal end 82b of the vibration transmission portion 82 define the longitudinal axis L. The longitudinal axis L of the vibration transmission portion 82 may be formed substantially straight from the distal end 82a to the proximal end 82b, may be formed substantially straight on a proximal end side of a proximal end of the end effector 94 described below or may be bent at the end effector 94 including the distal end 82*a*.

A distance between the distal end 82*a* and the proximal end 82*b* of the vibration transmission portion 82, i.e., the length of the vibration transmission portion 82 is formed longer than the maximum outer diameter (the maximum outer diameter of the columnar rod) D of the vibration transmission portion 82. A connection portion 92 to which the transducer unit 24 is fixed is formed at a proximal end portion including the proximal end 82*b* of the vibration transmission portion 82. The connection portion 92 is formed as a male screw, for example.

The end effector 94 which is configured to appropriately treat the biological tissue when ultrasonic vibration is transmitted from the proximal end 82*b* to the distal end 82*a* is formed at the distal end portion including the distal end 82*a* of the vibration transmission portion 82. The end effector 94 is formed in an appropriate shape. The end effector 94 described herein has a distal end bent by taking visibility into account. Furthermore, the end effector 94 is formed in a predetermined shape which meshes with the jaw 46.

The length of the vibration transmission portion 82 is adjusted according to the frequency (wavelength) at which the transducer unit 24 generates vibration. Particularly, the length of the vibration transmission portion 82 is adjusted so that the proximal end 82*b* of the vibration transmission portion 82 becomes the antinode position of vibration which vibrates (vertically vibrates) the proximal end 82*b* along the longitudinal axis L, when vibration is transmitted from the proximal end 82*b* to the distal end 82*a* of the vibration transmission portion 82.

In addition, similar to known probes, a portion which appropriately amplifies the amplitude when the vibration is transmitted by tapering part of the shape of the vibration transmission portion 82 in a tapered shape whose diameter becomes smaller toward the distal end side is optimally formed from the proximal end 82*b* to the proximal end of the end effector 94.

The engagement member 84 is fixed to and/or near an outer circumference at the position which is the node P of the vibration which does not vibrate when the vibration is transmitted from the proximal end 82*b* to the distal end 82*a* of the vibration transmission portion 82. Hence, the engagement member 84 is fixed to the outer circumferential surface of the vibration transmission portion 82 within a range of a region A illustrated in FIG. 5B.

Figure 5A:
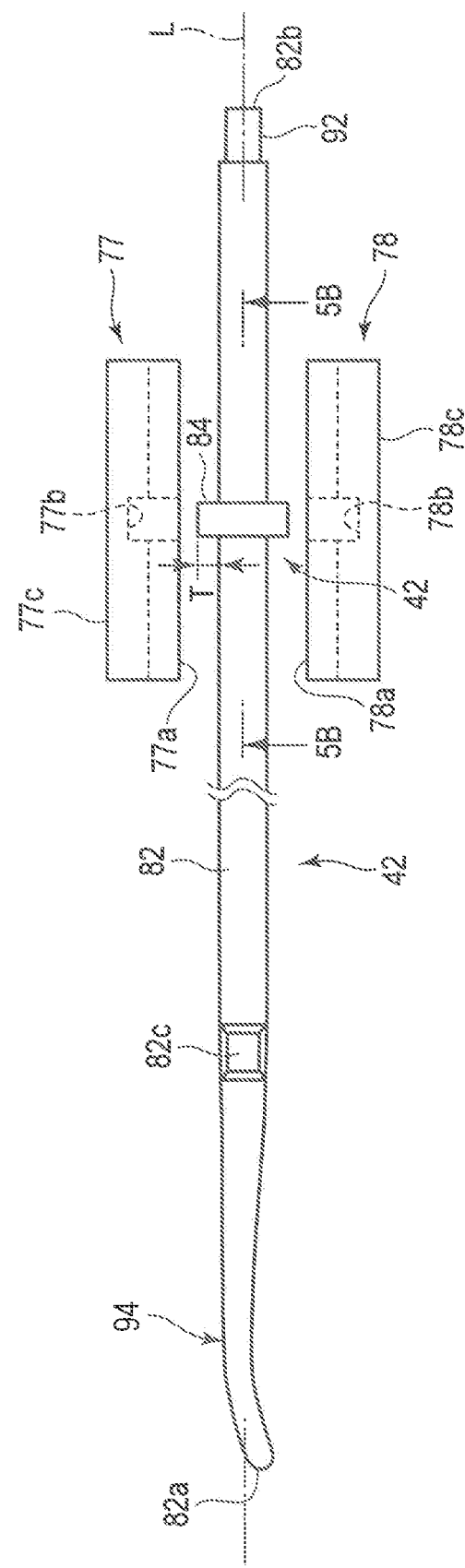
FIG. 5A is a schematic view illustrating a state where an engagement member is fixed to an appropriate position of an outer circumference of the vibration transmission portion of the probe of the shaft of the treatment instrument, and then the holder is disposed on an outer side of the engagement member in the treatment system according to the first embodiment.
Figure 5B:
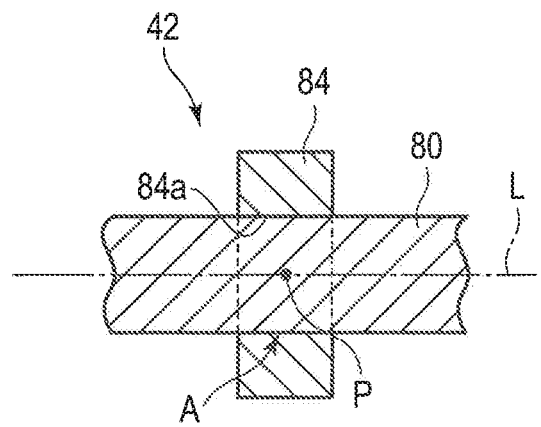
FIG. 5B is a cross-sectional view of the vibration transmission portion and the engagement member along a 5B-5B line including a longitudinal axis in FIG. 5A.
Figure 5C:
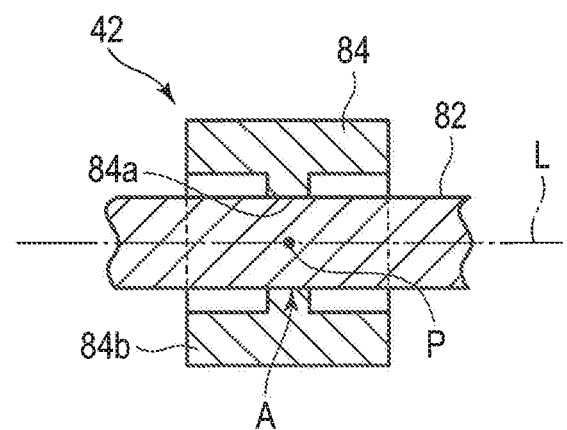
FIG. 5C illustrates a modified example of a cross-sectional view of the vibration transmission portion and the engagement member along the 5B-5B line including the longitudinal axis in FIG. 5A.

In addition, the engagement member 84 illustrated in FIG. 5C includes a cylindrical body 84*b* in a direction along the longitudinal axis L. An outer circumferential surface of the cylindrical body 84*b* is formed coplanarly with the outer circumferential surface of the engagement member 84. On the other hand, an inner circumferential surface of the cylindrical body 84*b* is at a radially outside of a through-hole 84*a*. In this case, a range A in which the engagement member 84 is fixed to the outer circumferential surface of the vibration transmission portion 82 is a portion except the cylindrical body 84*b*.

Figure 3B:
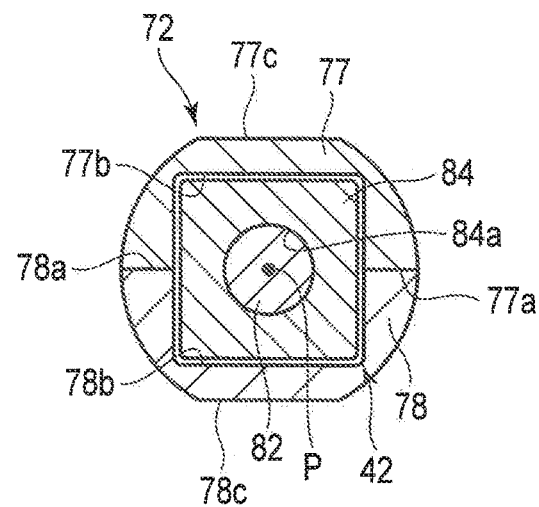
FIG. 3B is a schematic horizontal cross-sectional view along a 3B-3B line in FIG. 3A.
Figure 4:
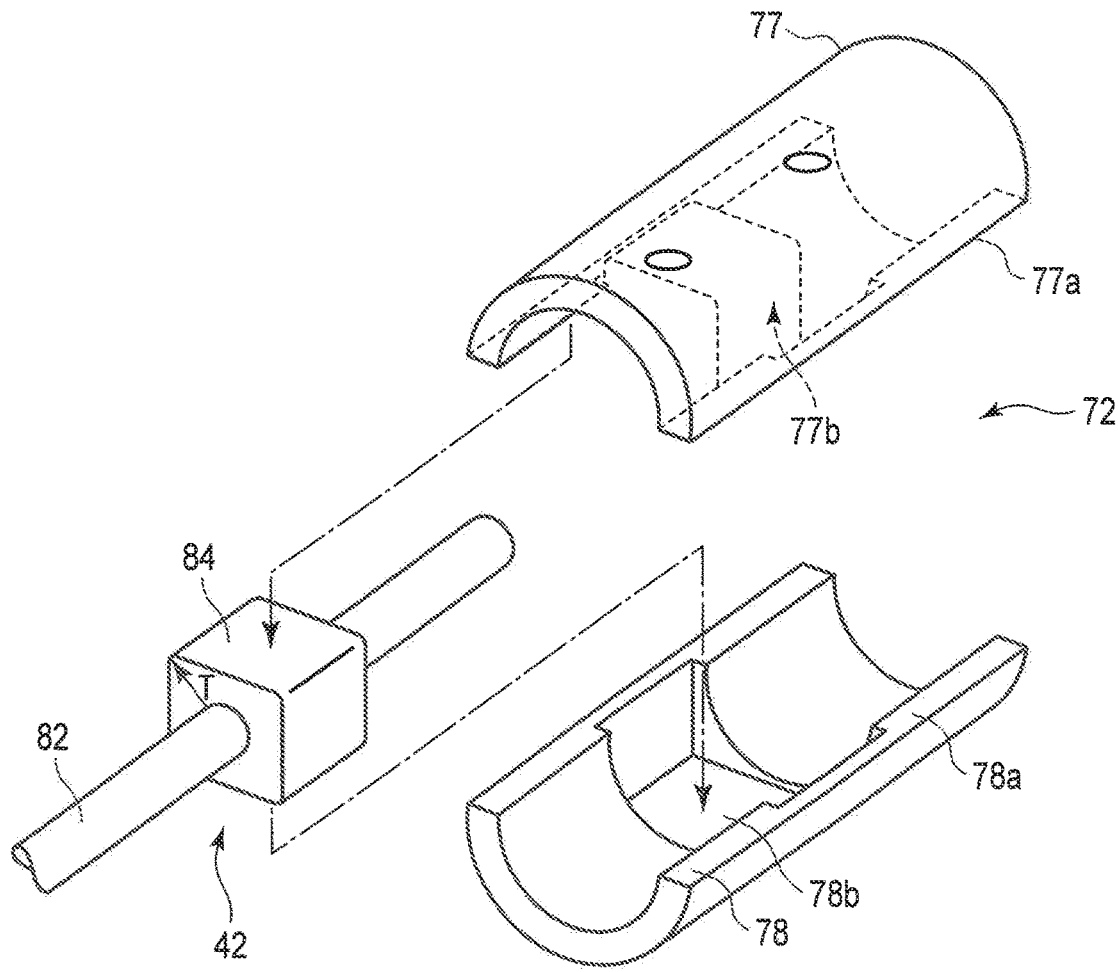
FIG. 4 is a schematic view illustrating a vibration transmission portion of the probe of the shaft of the treatment instrument of the treatment system according to the first embodiment.

The engagement member 84 is supported by the cylindrical portion (exterior member) 44. Hence, the probe 42 is supported by the cylindrical portion 44. The engagement member 84 is formed in a shape which prevents unintentional movement in and rotation around the axial direction of the longitudinal axis L with respect to the cylindrical portion 44. Hence, an outer rim of the engagement member 84 regulates rotation with respect to the cylindrical portion 44, and therefore is formed in a shape other than a circular shape. As illustrated in FIGS. 3A and 3B, an outer shape of the engagement member 84 is formed in a substantially cuboid shape, for example. The engagement member 84 is disposed at a portion of the vibration transmission portion 82 having substantially the same outer diameter as the outer diameter D of the columnar rod, and therefore has the through-hole 84*a* of a circular shape which is the same as or slightly smaller than the outer diameter D of the columnar rod. That is, the through-hole 84*a* of the engagement member 84 allows the vibration transmission portion 82 to be disposed on the inside.

The engagement member 84 is fixed firmly to the outer circumference of the vibration transmission portion 82 by various fixing methods or a combination thereof described below, and is supported firmly with respect to the cylindrical portion 44, and a material which hardly absorbs vibration is used for the engagement member 84. It is preferable that a metal material is used for the engagement member 84. It is preferable that an aluminum alloy material is used as, for example, a metal material for the engagement member 84. Furthermore, it is preferable to use duralumin having high strength among aluminum alloy materials for the engagement member 84. In addition, it is also preferable to use super duralumin or extra super duralumin different from duralumin for the engagement member 84. Furthermore, it is also preferable to use titanium or a titanium alloy for the engagement member 84. The engagement member 84 is formed by a material having a damping rate of ultrasonic vibration which is the same as that of the vibration transmission portion 82 or smaller than that of the vibration transmission portion 82. Therefore, it is not suitable to use for the engagement member 84 a rubber material or a general resin material having a higher damping rate and lower rigidity than those of the vibration transmission portion 82. In addition, it is better to avoid using for the engagement member 84 a material of a great damping rate such as part of iron, a stainless alloy material or a magnesium alloy material even in a case of metal materials. These materials readily absorb vibration and therefore readily generate heat as a result, and have a problem that the materials hardly hold an extrapolation member.

In this regard, for example, a stainless steel alloy or a magnesium alloy material also includes a material of low vibration absorption. Hence, by selecting a material of a low vibration damping rate even in a case of a seemingly same alloy material, it is optimal to form the engagement member 84. Similarly, physically speaking, another inorganic material such as ceramic or glass, or a resin material such as PPS (polyphenylene sulfide) having low acoustic attenuation (low damping) and high rigidity and hardness (high rigidity) can be used for the engagement member 84 depending on vibration conditions.

In addition, the columnar rod may be machined after the engagement member 84 is fixed, and the vibration transmission portion 82 of desired shape may be formed. Alternatively, the columnar rod may be machined before the engagement member 84 is fixed; the vibration transmission portion 82 of the desired shape may be formed and then the engagement member 84 may be fixed to the vibration transmission portion 82. Furthermore, at an intermediate stage of machining of the columnar rod, the engagement member 84 may be fixed to the vibration transmission portion 82.

As illustrated in FIGS. 3A to 5A, the holder 72 includes a first divided body 77 and a first divided body 78. The first divided body 77 and the first divided body 78 are each formed in a substantially half-pipe shape. Hence, the holder 72 is formed in a cylindrical shape by fitting a rim portion 77a of the first divided body 77 and a rim portion 78a of the first divided body 78.

The first divided body 77 and the first divided body 78 have recess grooves 77b and 78b to which the engagement member 84 is fitted. The recess grooves 77b and 78b face each other, so that the first divided body 77 and the first divided body 78 hold the engagement member 84 in cooperation. Hence, the holder 72 is disposed on the outer side of the vibration transmission portion 82.

For example, the outer circumference of the holder 72 includes a pair of planes 77c and 78c. Hence, the plane 77c of the first divided body 77 is fitted to the inner circumferential surface of the movable cylindrical portion 74, and the plane 78c of the second divided body 78 is fitted to the inner circumferential surface of the movable cylindrical portion 74, so that the holder 72 is fitted to the movable cylindrical portion 74. The movable cylindrical portion 74 is supported at the rotation operation knob 58 by the known mechanism.

Next, a fixing method in a case where the engagement member 84 is fixed to an appropriate position on the outer circumference of the vibration transmission portion 82 will be briefly described.

As illustrated in FIG. 6, the vibration transmission portion 82 is formed. First, the columnar rod made of a titanium alloy material and having the appropriate length is prepared. The length of the columnar rod is formed substantially equivalently to or slightly longer than the length of the vibration transmission portion 82 which is an end product. Furthermore, the same an outer diameter portion of the outer diameter of the vibration transmission portion 82 which is the end product as the outer diameter D of the columnar rod is preferably formed long as much as possible. In this case, it is possible to suppress material cost of the vibration transmission portion 82 of the probe 42, and reduce a machining amount. The probe 42 according to the present embodiment is in a state where a part of the outer circumference of the engagement member 84 is at a distance T (see FIG. 4) from the outer circumferential surface of the vibration transmission portion 82. Consequently, it is possible to save the material corresponding to the distance T in the radial direction compared to a conventional vibration transmission portion, and reduce the machining amount.

The outer circumferential surface of the columnar rod is formed as an appropriate smooth columnar surface. The vibration transmission portion 82 is formed symmetrically with respect to the longitudinal axis L, and a cross section perpendicular to the longitudinal axis L is formed in a circular shape about the longitudinal axis L. Hence, the vibration transmission portion 82 is formed symmetrically with respect to the longitudinal axis L. Thus, the vibration transmission portion 82 has high symmetry, so that, when vibration transmits from the proximal end 82b to the distal end 82a of the vibration transmission portion 82, it is possible to prevent occurrence of horizontal vibration and to stabilize the vibration.

In addition, the radius of the columnar rod is formed equivalently to or slightly larger than the radius at a position of the end effector 94 which is assumed by the vibration transmission portion 82 to be the farthest from the longitudinal axis L assuming that the columnar rod is cut.

Hereinafter, an example where the engagement member 84 is fixed to a predetermined position of the vibration transmission portion 82 (i.e., to and/or near the position which becomes the node P of the vibration when it is assumed that the vibration is transmitted) by shrink-fitting will be described.

It is assumed that the transducer unit 24 is temporarily connected to the proximal end 82b of the columnar rod. In this case, the engagement member 84 is fixed to and/or near the outer circumference at the position which becomes the node P of the vibration when it is assumed that the transducer unit 24 generates vibration, and the vibration is transmitted to the vibration transmission portion 82. When a plurality of nodes of vibration are formed, the engagement member 84 is fixed to and/or near the outer circumference at the position which becomes the node P of vibration on the most proximal end side, for example.

It is preferable that the engagement member 84 is fixed to the position which is the node P of the vibration when the vibration is transmitted. In this regard, the node P of the vibration is defined as a point. The engagement member 84 has the appropriate thickness along the longitudinal axis L, and therefore the engagement member 84 is fixed not only to the outer circumference at the position which becomes the node P of the vibration but also to the position continuing to the vicinity of the outer circumference.

Furthermore, it is preferable that the engagement member 84 is fixed not to the outer circumference at the position which is the node P of vibration, but to the vicinity of the outer circumference. That is, the engagement member 84 is not only fixed to the outer circumference at the position which becomes the node P of the vibration, but also allowed to be shifted more or less.

When appropriate heat is applied to the engagement member 84, the engagement member 84 slightly expands. Hence, the inner diameter of the through-hole 84a becomes slightly larger. In this state, the vibration transmission portion 82 is inserted in the through-hole 84a of the engagement member 84, the center of the through-hole 84a of the engagement member 84 in the direction along the longitudinal axis L is disposed on and near the outer circumference at the position which becomes the node P of the vibration of the vibration transmission portion 82. When the engagement member 84 is cooled in this state, the engagement member 84 is fixed to the position including the outer circumference at the position which becomes the node P of the vibration of the vibration transmission portion 82.

In this case, the outer circumferential surface of the columnar rod is formed as the appropriate smooth columnar surface. The vibration transmission portion 82 is formed symmetrically with respect to the longitudinal axis L and has high symmetry, so that it is possible to stabilize the vibration when the ultrasonic vibration is transmitted. Furthermore, there is no interposed object such as an adhesive which is likely to influence transmission of vibration between the vibration transmission portion 82 and the engagement member 84. Consequently, it is possible to suppress loss of the vibration transmitting from the proximal end 82b to the distal end 82a of the vibration transmission portion 82.

Furthermore, the end effector 94 is machined in an appropriate shape and is formed in a desired shape. The engagement member 84 may be disposed on the outer circumference of the vibration transmission portion 82, and then the end effector 94 may be formed. The end effector 94 may be formed at the vibration transmission portion 82, and then the engagement member 84 may be disposed on the outer circumference of the vibration transmission portion 82. Alternatively, in the middle of a process of forming the end effector 94 at the vibration transmission portion 82, the engagement member 84 may be disposed on the outer circumference of the vibration transmission portion 82.

Although the probe 42 is formed in this way, the outer diameter from the distal end of the engagement member 84 to the distal end of the end effector 94 is formed substantially equivalently to that of the conventional probe. Consequently, the strength of the vibration transmission portion 82 can be maintained at the same level as that of a conventional vibration transmission portion. That is, the strength of the end effector 94 can be maintained at the same level as that of a conventional end effector.

The probe 42 formed in this way is disposed in the housing 32 as illustrated in FIGS. 1 and 2.

Furthermore, the connection portion (female screw) 92 at the proximal end 82b of the vibration transmission portion 82 of the probe 42 is screwed to the connection portion (male screw) 66a at the distal end of the transducer side transmission portion 66 of the transducer unit 24. In this case, the transducer unit 24 is fixed to the housing 32. The vibration transmission portion 82 is electrically connected to the transducer side transmission portion 66. Hence, when the first button 26a is pressed, the end effector 94 of the vibration transmission portion 82 is used as the high frequency electrode. Furthermore, when the second button 26b is pressed, the end effector 94 of the vibration transmission portion 82 is used as the high frequency electrode, and ultrasonic vibration generated by the transducer 64 is transmitted. Hence, while the end effector 94 is used as the high frequency electrode, the end effector 94 vertically vibrates in the axial direction of the longitudinal axis L.

As described above, the following can be said for the treatment instrument 22 according to the present embodiment.

For example, a titanium material (titanium alloy material) used for the vibration transmission portion 82 is an expensive material itself, is difficult to machine, and therefore is known to be highly costly. Conventionally, when, for example, a columnar rod whose maximum outer diameter is 8 mm is machined to form a probe, a maximum outer diameter of an engagement portion which engages with an exterior member is maintained at or close to 8 mm. On the other hand, for example, a portion (e.g., a portion on the distal end side) except the engagement portion has the outer diameter of 4 mm and has only ¼ of an area ratio left compared to a case where the maximum outer diameter is 8 mm. In this case, ¾ of the area ratio of the columnar rod needs to be machined and removed. Furthermore, the engagement portion is usually formed near a proximal end portion of the probe. Therefore, it is easy to imagine that, when the probe becomes longer, loss of the material is greater.

According to the present embodiment, the engagement member 84 can be fixed to the outer circumference of the vibration transmission portion 82 later to form the probe 42. Consequently, it is not necessary to perform machining such as cutting of the material corresponding to the distance T between the columnar rod in order to form the engagement member 84. Consequently, it is possible to omit cutting of the material corresponding to the distance T between the outer circumferential surface of the columnar rod and a part of the outer circumference of the engagement member 84. It is possible to reduce the machining amount of the columnar rod which is the material as much as possible, and form the probe 42. Although, for example, the columnar rod whose maximum outer diameter is 8 mm is conventionally machined, the columnar rod whose outer diameter is 4 mm can be used in advance to form the probe 42. Consequently, according to the probe 42 which adopts the structure according to the present embodiment, it is possible to reduce loss of the material as much as possible, and suppress machining cost, too. Consequently, according to the present embodiment, it is possible to provide the probe 42 which enables reduction of the machining amount as much as possible, and can engage with, for example, the exterior member such the housing 32 and/or the rotation knob 58.

In addition, although the probe 42 is formed in this way, the outer diameter from the distal end of the engagement member 84 to the distal end of the end effector 94 is formed substantially equivalently to that of the conventional probe. Consequently, the strength of the end effector 94 of the vibration transmission portion 82 can be maintained at the same level as that of the end effector.

MODIFIED EXAMPLE 1

Figure 7A:
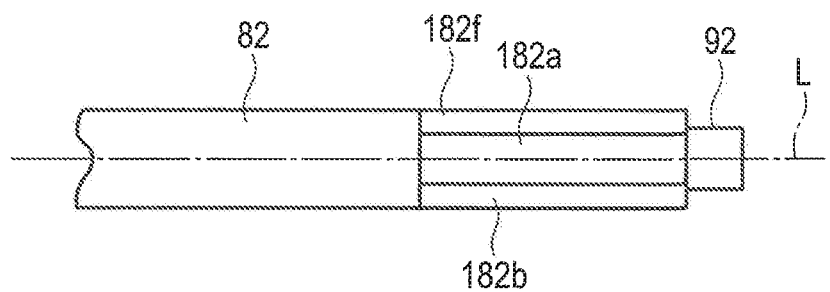
FIG. 7A is a schematic view illustrating a vicinity of proximal end portion of a vibration transmission member of the probe according to a modified example of the first embodiment.
Figure 7B:
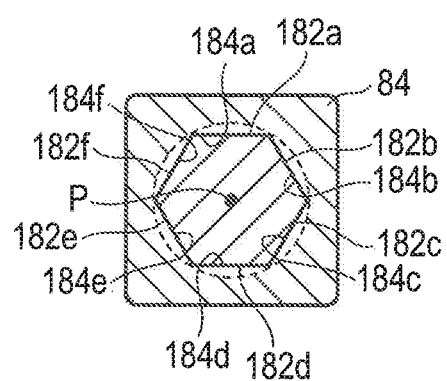
FIG. 7B is a schematic cross-sectional view illustrating a state where the engagement member is fitted near the proximal end portion of the vibration transmission member illustrated in FIG. 7A.

As illustrated in FIGS. 7A and 7B, a position (an outer circumferential surface at the position which becomes the node P of vibration) to which the engagement member 84 is attached on the outer circumferential surface of the vibration transmission portion 82 is optionally machined and formed in a polygonal shape. In this case, the through-hole 84a of the engagement member 84 is formed in the same polygonal shape. In this regard, the polygonal shape is a regular hexagonal shape, and the vibration transmission portion 82 includes first to six planes 182a to 182f on the outer circumferential surface. Hence, the outer circumference of the vibration transmission portion 82 and the first to sixth planes 184a to 184f of the inner circumferential surface of the through-hole 84a of the engagement member 84 are fitted by a fitting structure which places planes into contact with each other. Hence, it is possible to prevent the engagement member 84 from moving in a circumferential direction around the longitudinal axis L with respect to the vibration transmission portion 82 in a state where the engagement member 84 is fixed to the vibration transmission portion 82.

Figure 8A:
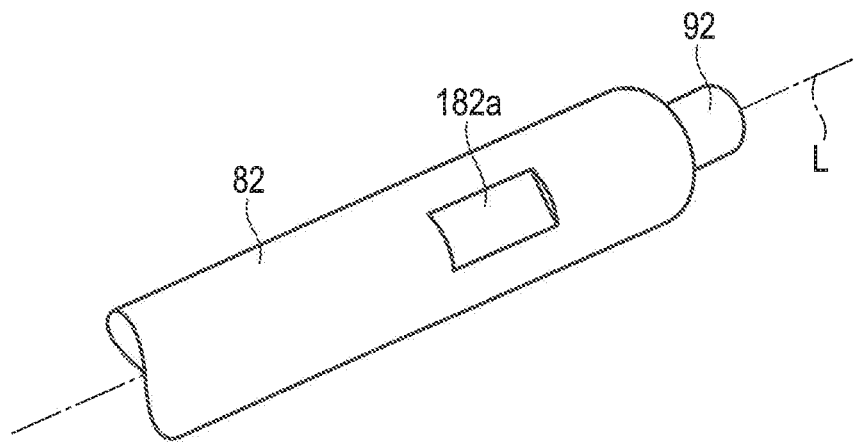
FIG. 8A is a schematic perspective view illustrating a vicinity of the proximal end portion of the vibration transmission member of the probe according to the modified example of the first embodiment.
Figure 8B:
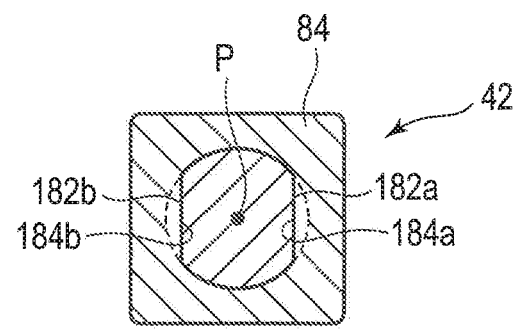
FIG. 8B is a schematic cross-sectional view illustrating a state where the engagement member is fitted near the proximal end portion of the vibration transmission member illustrated in FIG. 8A.

FIGS. 7A and 7B illustrate a structure which enhances holding strength of the engagement member 84 with respect to the vibration transmission portion 82 in terms of a mechanical structure in the entire circumference of the vibration transmission portion 82. FIGS. 8A and 8B illustrate an example of a structure which enhances holding strength of the engagement member 84 with respect to the vibration transmission portion 82 in terms of a mechanical structure in a part of the vibration transmission portion 82. As illustrated in FIGS. 8A and 8B, the vibration transmission portion 82 includes a pair of planes 182a and 182b to which normal vectors are directed in opposite directions. A first fitting plane 184a of the engagement member 84 is fitted to the first plane 182a, and a second fitting plane 184b of the engagement member 84 is fitted to the second plane 182b.

Figure 9A:
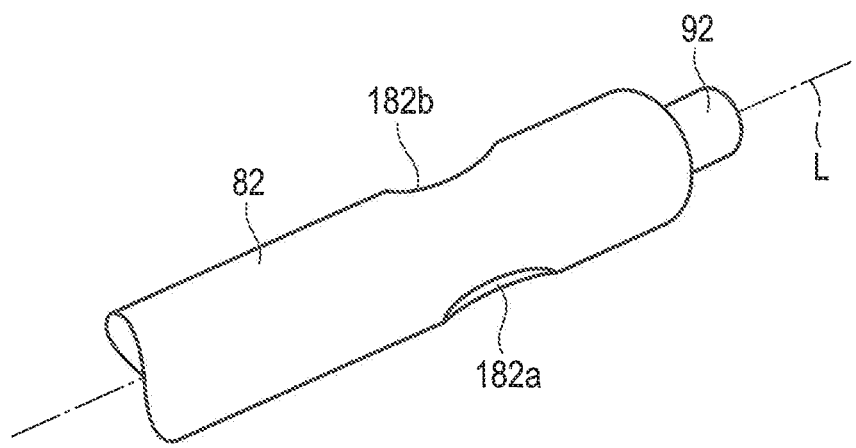
FIG. 9A is a schematic perspective view illustrating the vicinity of the proximal end portion of the vibration transmission member of the probe according to the modified example of the first embodiment.
Figure 9B:
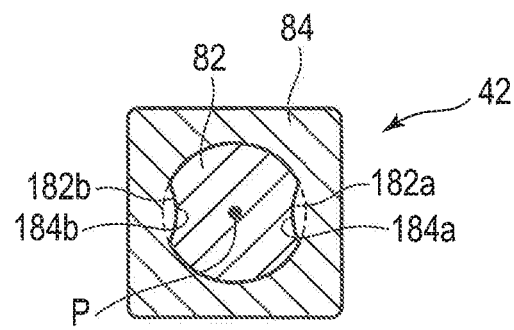
FIG. 9B is a schematic cross-sectional view illustrating a state where the engagement member is fitted near the proximal end portion of the vibration transmission member illustrated in FIG. 9A.

Similarly, FIGS. 9A and 9B illustrate an example where a curved surface is used instead of the planes illustrated in FIGS. 8A and 8B. Even this shape can enhance the holding strength of the engagement member 84 with respect to the vibration transmission portion 82 in terms of the mechanical structure.

MODIFIED EXAMPLE 2

When the engagement member 84 is fixed to the vibration transmission portion 82, the engagement member 84 can be fixed to the vibration transmission portion 82 by way of adhesion. By, for example, using an anaerobic adhesive cured by blocking air, the vibration transmission portion 82 and the engagement member 84 are fixed highly strongly. Furthermore, an adhesion time of the anaerobic adhesive can be shortened compared to, for example, an epoxy adhesive, so that it is possible to reduce an assembly time. In addition, the anaerobic adhesive is more readily cured as the thickness is thinner. Hence, the anaerobic adhesive only needs to be formed very thin between the vibration transmission portion 82 and the engagement member 84. Consequently, the anaerobic adhesive hardly cause occurrence of vibration loss between the vibration transmission portion 82 and the engagement member 84.

MODIFIED EXAMPLE 3

When the vibration transmission portion 82 and the engagement member 84 are both formed by the same type of a material such as a titanium alloy material, the vibration transmission portion 82 and the engagement member 84 can be fixed highly strongly by welding such as laser welding. In this case, it is preferable to remove a residual stress produced by welding between the vibration transmission portion 82 and the engagement member 84 by annealing or the like.

Even in a case of different types of materials which are a titanium alloy material for the vibration transmission portion 82 and an aluminum alloy material for the engagement member 84, the vibration transmission portion 82 and the engagement member 84 are fixed highly strongly by brazing.

When the engagement member 84 is formed by a material of a relatively low melting point such as the aluminum alloy material, the engagement member 84 can be formed on the vibration transmission portion 82 by casting. In this case, the engagement member 84 is formed integrally with the vibration transmission portion 82, so that it is possible to obtain high adhesion.

When the engagement member 84 is formed by a material which deforms at a lower temperature than the vibration transmission portion 82, the engagement member 84 can be formed on the vibration transmission portion 82 by, for example, an HIP method (hot isostatic pressing method). In this case, the engagement member 84 is formed integrally with the vibration transmission portion 82, so that it is possible to obtain high adhesion.

When the engagement member 84 is formed by a material which is softer than that of the vibration transmission portion 82, the engagement member 84 can be formed on the vibration transmission portion 82 by, for example, a CIP method (cold isostatic pressing method). In this case, the engagement member 84 is formed around the vibration transmission portion 82 at a room temperature, so that it is possible to prevent an influence of the temperature.

The engagement member 84 is directly formed on the outer circumference of the vibration transmission portion 82 using molten metal powders, laser powder metallurgy or the like by a known 3D molding technique and can be formed in an appropriate complicated shape.

MODIFIED EXAMPLE 4

Figure 10A:
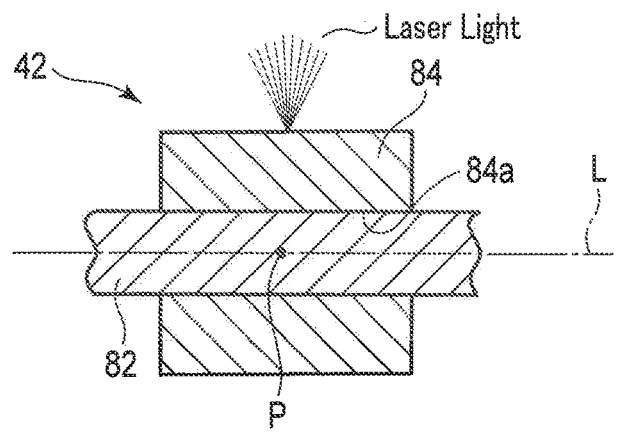
FIG. 10A is a schematic view illustrating a state where an outer circumferential surface of the engagement member is irradiated with laser light in a state where an engagement member of a cylindrical shape is disposed near the proximal end portion of the vibration transmission member of the probe according to the modified example of the first embodiment.
Figure 10B:
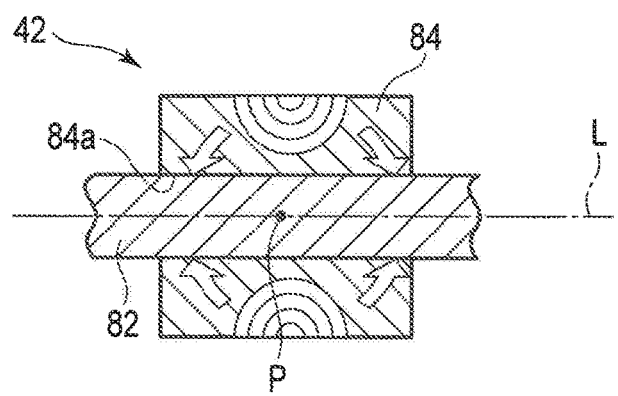
FIG. 10B is a schematic view illustrating a state where the irradiation of the laser light illustrated in FIG. 10A changes a crystal state of an irradiated position, bulges the irradiated position, produces a stress in the engagement member, and holds the outer circumferential surface of the vibration transmission portion at a distal end portion and the proximal end portion along the longitudinal axis of an inner circumferential surface of the engagement member.

In addition, as illustrated in FIGS. 10A and 10B, a part of the engagement member 84 may be plastically deformed to exhibit a holding force for the vibration transmission portion 82. As illustrated in, for example, FIG. 10A, the engagement member 84 of the cylindrical shape is disposed on the outer circumference of the vibration transmission portion 82. Furthermore, the outer circumferential surface of the engagement member 84 is irradiated with laser light to change a crystal structure of the engagement member 84. More specifically, the outer circumference of the engagement member 84 is heated and expanded along the circumferential direction. Hence, as illustrated in FIG. 10B, a stress which holds the outer circumference of the vibration transmission portion 82 acts on positions on a distal end side and a proximal end side adjacent to a position irradiated with the laser light. According to the plastic machining, the engagement member 84 can be appropriately fixed to the outer circumference of the vibration transmission portion 82.

Figure 10C:
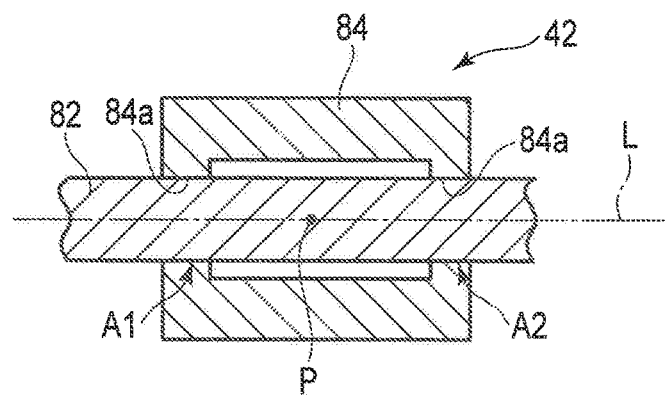
FIG. 10C illustrates a modified example of the example illustrated in FIGS. 10A and 10B, and is a schematic view illustrating a state where the vibration transmission portion is held by an engagement portion at a position apart along the longitudinal axis from the outer circumferential surface at a position which becomes a node of vibration.

In addition, it is also preferable that, as illustrated in FIG. 10C, areas A1 and A2 shifted along the longitudinal axis L from a position corresponding to the outer circumference of the node P of vibration are held by the engagement member 84. In this case, the engagement member 82 holds the vibration transmission portion 82 at a plurality of positions, so that it is possible to enhance the holding force. Furthermore, the engagement member 84 holds the position which hedges the node P of the vibration along the longitudinal axis L of the vibration transmission portion 82. Consequently, it is possible to prevent vibration in the radial direction of the vibration transmission portion 82 from transmitting to the outside. Furthermore, it is possible to allow the vibration transmission portion 82 to be displaced in the radial direction perpendicular to the longitudinal axis L of the vibration transmission portion 82 when ultrasonic vibration is transmitted to the vibration transmission portion 82.

MODIFIED EXAMPLE 5

Figure 11A:
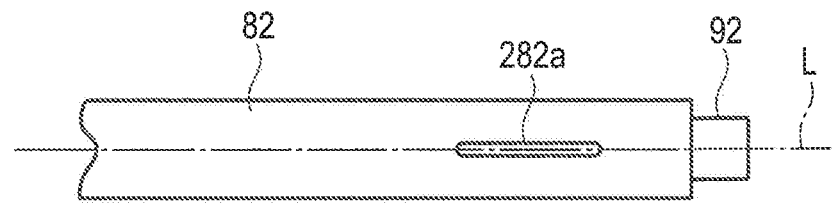
FIG. 11A is a schematic view illustrating a vicinity of the proximal end portion of the vibration transmission member of the probe according to the modified example of the first embodiment.
Figure 11B:
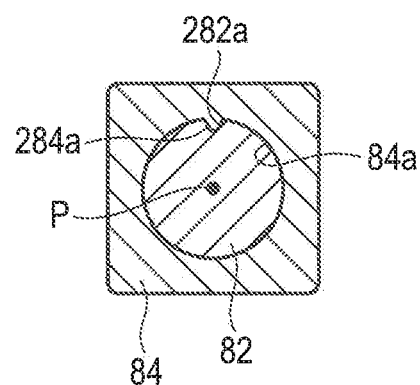
FIG. 11B is a schematic cross-sectional view illustrating a state where the engagement member is fitted near the proximal end portion of the vibration transmission member illustrated in FIG. 11A.

As illustrated in FIGS. 11A and 11B, a recess groove 282a is formed in a part of the vibration transmission portion 82. In this case, it is preferable that a protrusion 284a is formed on the inner circumferential surface of the through-hole 84a of the engagement member 84. Hence, the protrusion 284a engages with the recess groove 282a, so that the engagement member 84 can be fixed to the vibration transmission portion 82 more firmly.

Figure 12A:
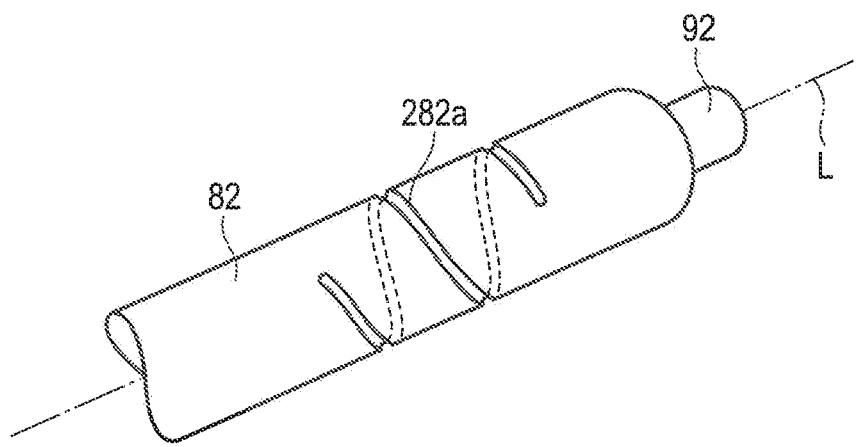
FIG. 12A is a schematic perspective view illustrating the vicinity of the proximal end portion of the vibration transmission member of the probe according to the modified example of the first embodiment.
Figure 12B:
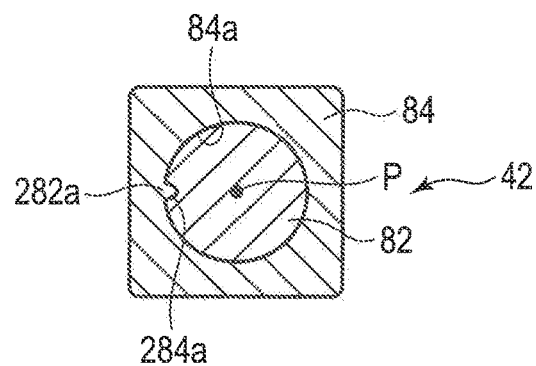
FIG. 12B is a schematic cross-sectional view illustrating a state where the engagement member is fitted near the proximal end portion of the vibration transmission member illustrated in FIG. 12A.

In addition, as illustrated in FIGS. 12A and 12B, the recess groove 282a and the protrusion 284a do not need to be formed in parallel to, i.e., straight with respect to the longitudinal axis L, and only need to be appropriately formed in a spiral shape.

Figure 13A:
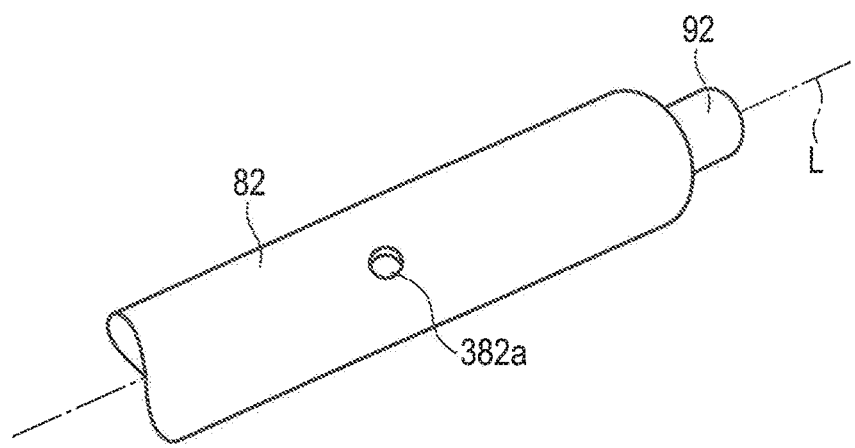
FIG. 13A is a schematic perspective view illustrating the vicinity of the proximal end portion of the vibration transmission member of the probe according to the modified example of the first embodiment.
Figure 13B:
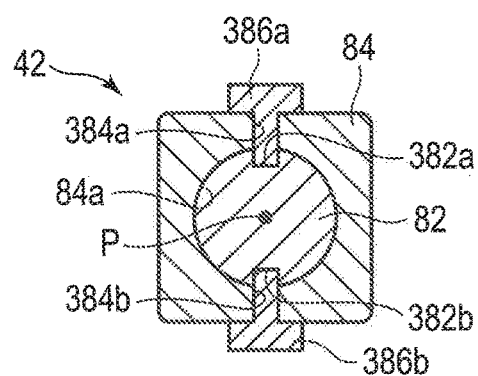
FIG. 13B is a schematic cross-sectional view illustrating a state where the engagement member and a pin are fitted near the proximal end portion of the vibration transmission member illustrated in FIG. 13A.

As illustrated in FIGS. 13A and 13B, when the engagement member 84 is fixed to the vibration transmission portion 82, auxiliary members such as a key and a pin can be used. In this case, it is possible to prevent heating in a case where the engagement member 84 is fixed to the vibration transmission portion 82 from causing an unintentional thermal influence on the engagement member 84 and the vibration transmission portion 82.

More specifically, the vibration transmission portion 82 includes, for example, a pair of recess holes 382a and 382b. The engagement member 84 includes through-holes 384a and 384b which continue to the recess holes 382a and 382b. The through-holes 384a and 384b are formed in the direction perpendicular to the longitudinal axis L. Furthermore, a first pin 386a is fixed to the through-hole 384a and the recess hole 382a, and a second pin 386b is fixed to the through-hole 384b and the recess hole 382b.

When recess grooves 482a and 482b are formed in the direction perpendicular to the longitudinal axis L of the vibration transmission portion 82 as illustrated in example in FIGS. 14A and 14B, for example, the engagement member 84 of a substantially U shape may be used. The engagement member 84 includes leg portions 484a and 484b. The leg portions 484a and 484b are fitted to the recess grooves 482a and 482*b*, so that the engagement member 84 is fixed to the vibration transmission portion 82.

MODIFIED EXAMPLE 6

Figure 15B:
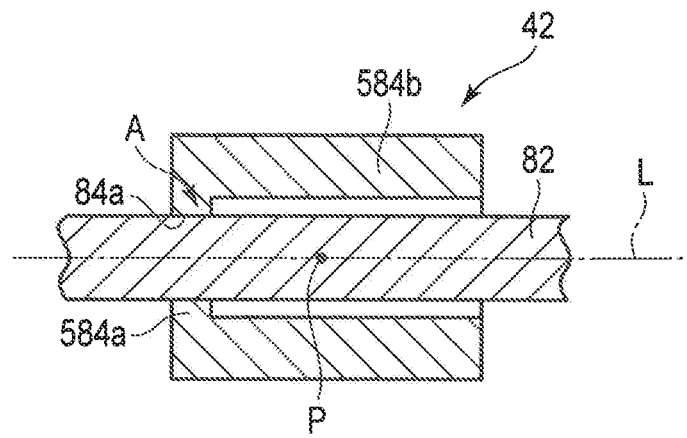
FIG. 15B is a schematic cross-sectional view illustrating a state where the engagement member is fitted near the proximal end portion of the vibration transmission member illustrated in FIG. 15A.

In an example illustrated in FIGS. 15A and 15B, the engagement member 84 is formed by sheet metal working. The engagement member 84 includes a hub 584*a* and a plurality of wings 584*b* which extend outward from the hub 584*a*. The engagement member 84 is formed by appropriately bending a plate of a cross shape including the opening 84*a*. Thus engagement member 84 is fitted to the appropriate holder 72 and is held.

When, for example, the outer circumference at the position shifted along the longitudinal axis L from the position which becomes the node P of vibration is held by the engagement member 84, it is possible to make vibration in the radial direction of the vibration transmission portion 82 hardly transmit to the outside.

MODIFIED EXAMPLE 7

Figure 16:
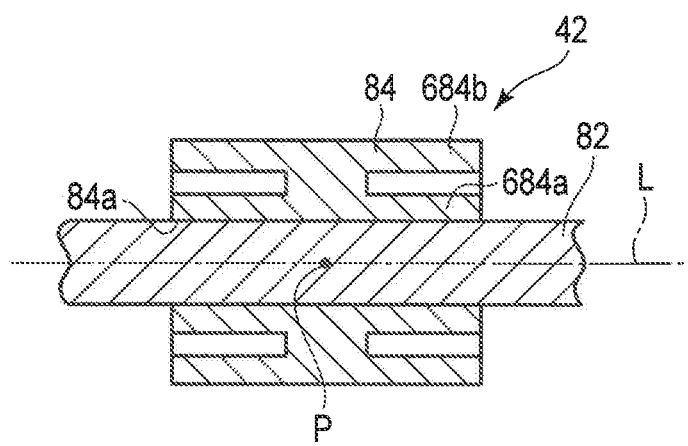
FIG. 16 is a schematic cross-sectional view illustrating a state where the engagement member is fixed near the proximal end portion of the vibration transmission member of the probe according to the modified example of the first embodiment.

In an example illustrated in FIG. 16, a part of the engagement member 84 is made thin. In this regard, the engagement member 84 includes an inner cylinder 884*a* which forms the through-hole 84*a*, and an outer cylinder 684*b* which is formed apart from the outer circumference of the inner cylinder 684*a*. The holder 72 is fitted to the outer circumferential surface of the outer cylinder 684*b*. The inner cylinder 684*a* and the outer cylinder 684*b* are apart, so that it is possible to make vibration to be transmitted to the vibration transmission portion 82 hardly transmit to the outside such as the holder 72.

As described above, there are permitted various methods for fixing, molding and disposing the engagement member 84 to and/or near the position of the outer circumference at the position which becomes the node P of vibration when ultrasonic vibration is transmitted to the vibration transmission portion 82, and forming the probe 42. The engagement member 84 is formed by the material having the damping rate of ultrasonic vibration which is the same as that of the vibration transmission portion 82 or smaller than that of the vibration transmission portion 82 by taking heat generation into account.

In addition, the outer shape of the engagement member 84 of the probe 42 has been described as a substantially cuboid shape, yet can be appropriate set in relation to the older 72.

Second Embodiment

Next, a second embodiment will be described with reference to FIGS. 17 to 18B. The present embodiment is a modified example of the first embodiment, and members which are the same members as or have the same functions as the members described in the first embodiment will be assigned the same reference numerals, and detailed description thereof will be omitted.

The first embodiment has described an example of a treatment instrument 22 which sandwiches a biological tissue between an end effector 94 of a vibration transmission portion 82 and a jaw 46 to perform treatment. However, an example of a treatment instrument 122 which is moved along a longitudinal axis L to perform treatment will be described. Furthermore, a rotation knob 58 is not disposed in a housing 32.

Figure 17:
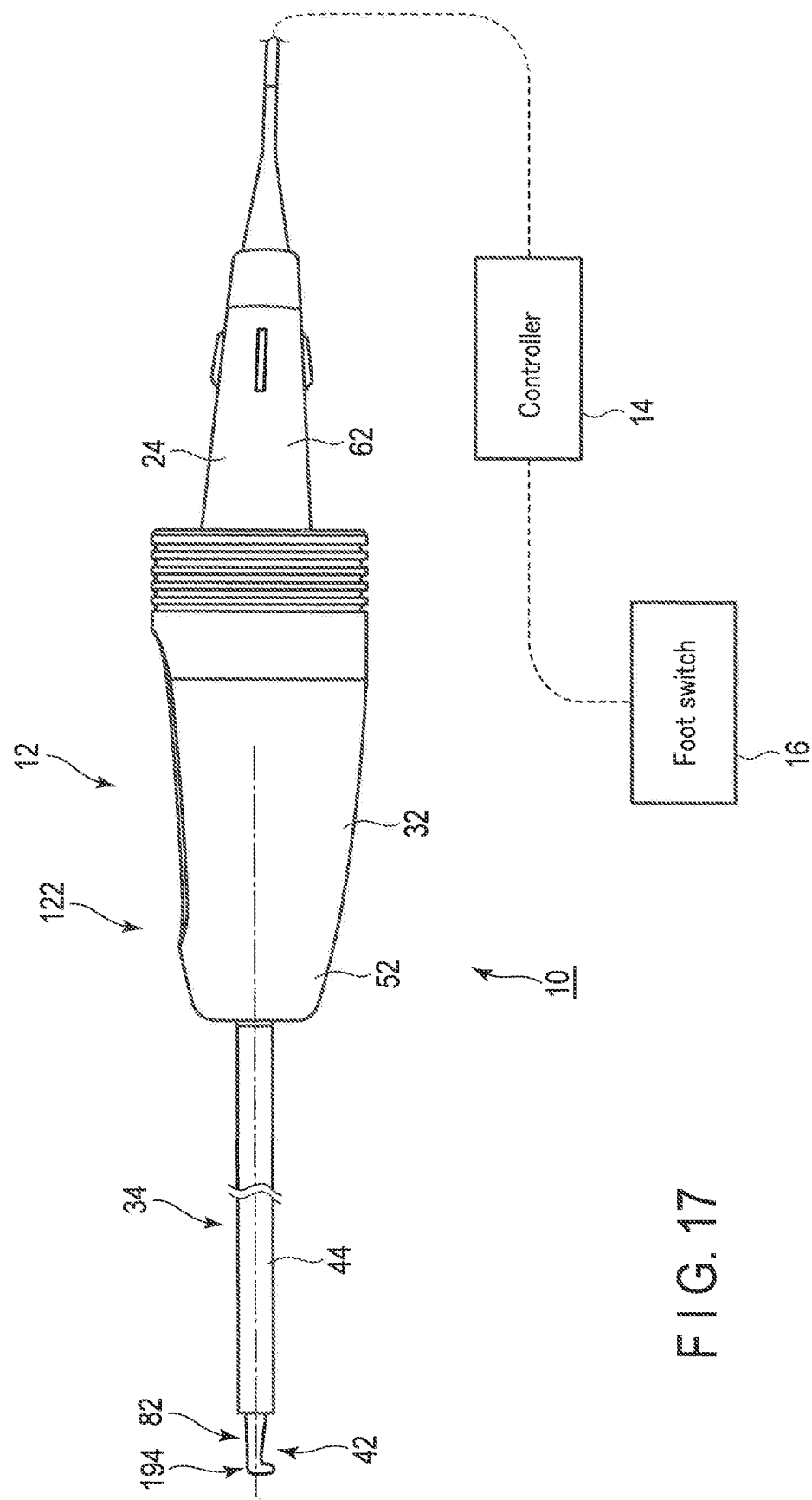
FIG. 17 is a schematic view illustrating a treatment system according to a second embodiment.

As illustrated in FIG. 17, a treatment system 10 includes a treatment device 12, a controller 14 which includes a power supply and a foot switch 16. The treatment device 12 includes the treatment instrument 122, and a transducer unit 24 which is fixed to the treatment instrument 122 to be used.

When the foot switch 16 is pressed in a state where a user (doctor) places an end effector 194 in contact with the biological tissue, the treatment instrument 122 illustrated in FIG. 17 transmits ultrasonic vibration to a probe 42 of the treatment instrument 122. Furthermore by moving the probe 42 along the longitudinal axis L in a state where the ultrasonic vibration transmits to the probe 42, the user can cut the biological tissue.

Similar to the description of the first embodiment, the probe 42 of treatment instrument 122 includes the vibration transmission portion 82 and an engagement member 84. The vibration transmission portion 82 and the engagement member 84 are formed as separate bodies.

Figure 18B:
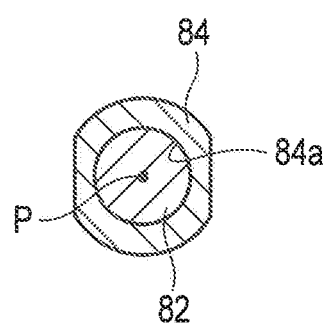
FIG. 18B is a schematic cross-sectional view along an 18B-18B line in FIG. 18A.

A distal end 82*a* to a proximal end 82*b* of the vibration transmission portion 82 illustrated in FIGS. 18A and 18B are within a range of a maximum outer diameter D of a columnar rod. Consequently, by, for example, performing cutting machining, it is possible to form the end effector 194 of an appropriate shape. In this case, it is optimal to form the end effector 194 on a distal end side of a distalmost end position among positions which become a node P of vibration when vibration is transmitted to the vibration transmission portion 82.

Furthermore, as illustrated in FIGS. 18A and 18B, the engagement member 84 is fixed, molded and disposed at and/or near the position of the outer circumference at the position which becomes the node P of vibration when ultrasonic vibration is transmitted to the vibration transmission portion 82 to form the probe 42.

Consequently, according to the present embodiment, it is possible to provide the probe 42 which enables reduction of the machining amount as much as possible, and can engage with, for example, an exterior member such a housing 32.

Furthermore, the vibration transmission portion 82 including the end effector 194 according to the present embodiment can be formed by simply cutting the columnar rod. In addition, by appropriately performing heat processing, the vibration transmission portion 82 can have appropriate strength, appropriate ductility and appropriate toughness.

In addition, the shape of the end effector 194 of the vibration transmission portion 82 of the probe 42 can be appropriately set to various treatment devices. In a case of, for example, a hook type which is one of the treatment devices which do not need the jaw 46, the end effector 194 can be set to a shape having a hook portion. In addition, the shape of the end effector 194 is naturally allowed to have various shapes. Hence, the vibration transmission portion 82, i.e., the probe 42 to which the common engagement member 84 is fixed can support a plurality of types of lineups. Each probe 42 allows the common engagement member 84 to be appropriately attached to the housing 32 with the holder 72 interposed therebetween.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
   a probe including:
   an elongated main body that is configured to transmit ultrasonic vibration, and
   an engagement member that is provided on an outer circumference of a position of the main body and/or in the vicinity of the outer circumference of the position of the main body,
   the position of the main body becoming a node of the ultrasonic vibration when the ultrasonic vibration is transmitted to the main body, and
   the engagement member being formed by a material of an identical to or smaller damping rate than a damping rate of the ultrasonic vibration in the main body; and
   an exterior member that includes a holder engaged with the engagement member and that is disposed on an outer side of the main body,
   the holder being configured to regulate movement of the engagement member in an axial direction of a longitudinal axis of the main body with respect to the holder, and being configured to regulate rotation of the engagement member in a direction around the longitudinal axis.

2. The treatment instrument according to claim 1, wherein:
   the main body is formed by titanium or a titanium alloy, and the engagement member is formed by an aluminum alloy.

3. The treatment instrument according to claim 2, wherein the aluminum alloy is one of duralumin, super duralumin and extra super duralumin.

4. The treatment instrument according to claim 1, wherein:
   an outer shape of the engagement member is formed in a shape other than a circular shape, and
   the engagement member is configured to regulate rotation with respect to the exterior member.

5. The treatment instrument according to claim 1, comprising a clearance between the engagement member and the holder.

6. The treatment instrument according to claim 1, wherein the engagement member includes a hole in which the main body is disposed inside.

7. The treatment instrument according to claim 6, wherein the outer circumference of the main body and an inner circumferential surface of the hole of the engagement member are fitted by a fitting structure.

8. The treatment instrument according to claim 1, wherein the engagement member is directly formed on the outer circumference of the main body.

9. The treatment instrument according to claim 1, wherein the engagement member is formed integrally with the main body.

10. The treatment instrument according to claim 1, wherein the engagement member covers the outer circumference of the position of the main body which becomes the node of the ultrasonic vibration when the ultrasonic vibration is transmitted to the main body, and allows displacement of the main body in a radial direction perpendicular to a longitudinal axis of the main body when the ultrasonic vibration is transmitted to the main body.

11. The treatment instrument according to claim 1, wherein:
    the main body includes:
    an end effector at a distal end portion of the main body, and
    a connection portion connected to a transducer unit configured to generate the ultrasonic vibration at a proximal end portion of the main body, and
    the distal end portion and the proximal end portion of the main body respectively correspond to antinode positions of vibration when the ultrasonic vibration is transmitted to the main body.

12. The treatment instrument according to claim 1, wherein the engagement member is formed by an inorganic material.

13. The treatment instrument according to claim 1, wherein the engagement member is formed by a highly rigidity and low damping resin material.

14. The treatment instrument according to claim 1, wherein the
    exterior member includes a gripping body which is configured to hold an outer side of the holder and which is configured to be gripped by a user.

15. The treatment instrument according to claim 1, wherein:
    the exterior member is a cylindrical shape having an electrical insulation property,
    the engagement member is engaged with an inside of the exterior member,
    the main body is formed by an elongated columnar rod, and includes a proximal end connected with a transducer unit configured to generate the ultrasonic vibration, and a distal end to which the ultrasonic vibration is configured to transmit,
    the columnar rod defines a maximum outer diameter of the main body, and
    at least a part of a distal end side and a proximal end side of the main body at a position at which the engagement member is provided is formed as an maximum outer diameter of the columnar rod or as an outer diameter slightly smaller than the maximum outer diameter of the columnar rod.

16. A treatment device comprising:
    the treatment instrument according to claim 1; and
    a transducer unit connected to a proximal end of the probe.

17. A method of assembling the treatment instrument according to claim 1, the method comprising:
    fixing the engagement member to the outer circumference of the position of the main body and/or in the vicinity of the outer circumference of the position of the main body;
    holding the engagement member with recess grooves of a first divided body and a second divided body which are each formed in a substantially half-pipe shape, fitting the first divided body and the second divided body, and forming the holder on an outer side of the main body; and
    supporting the holder to a housing configured to be gripped by a user.

18. An exterior member disposed on an outer side of an elongated main body and an engagement member on a probe including the main body configured to transmit ultrasonic vibration, and the engagement member provided on an outer circumference of a position of the main body and/or in the vicinity of the position of the main body, the position of the main body becoming a node of the ultrasonic vibration when the ultrasonic vibration is transmitted to the main body, the engagement member being formed by a material of an identical to or smaller damping rate than a damping rate of the ultrasonic vibration in the main body, the exterior member includes a holder engaged with the engagement member of the probe, and the holder is disposed on the outer side of the main body, the holder being configured to regulate movement of the engagement member in an axial direction of a longitudinal axis of the main body with respect to the holder, and being configured to regulate rotation of the engagement member in a direction around the longitudinal axis.

19. The exterior member according to claim 18, wherein:

the holder includes a first divided body and a second divided body, and the holder is formed in a cylindrical shape when a rim of the first divided body and a rim of the second divided body are fitted.

20. The exterior member according to claim 19, wherein:

the first divided body has a first recess groove to which the engagement member is fitted, the second divided body has a second recess groove to which the engagement member is fitted, and the first divided body and the second divided body hold the engagement member in cooperation.

\* \* \* \* \*